United States Patent

Kida et al.

[11] Patent Number: 5,989,624
[45] Date of Patent: Nov. 23, 1999

[54] METHOD FOR MANUFACTURING ELECTRODE

[75] Inventors: Masahito Kida, Aichi; Ryuji Inoue, Gifu; Takafumi Oshima, Aichi, all of Japan

[73] Assignee: NGK Spark Plug Co., Ltd., Nagoya, Japan

[21] Appl. No.: 09/134,047

[22] Filed: Aug. 14, 1998

[30] Foreign Application Priority Data

Aug. 14, 1997 [JP] Japan .................................. 9-233342

[51] Int. Cl.$^6$ .......................... G01N 27/407; B05D 5/12
[52] U.S. Cl. ........................ 427/125; 204/421; 204/424; 264/109; 264/122; 427/123; 427/126.3; 427/217; 427/372.2; 427/383.5
[58] Field of Search ..................... 204/421–429; 264/109, 122; 427/123, 125, 126.3, 217, 372.2, 383.5

[56] References Cited

U.S. PATENT DOCUMENTS

| | | | |
|---|---|---|---|
| 5,672,811 | 9/1997 | Kato et al. | 204/425 |
| 5,698,267 | 12/1997 | Friese et al. | 204/424 |
| 5,716,507 | 2/1998 | Tanaka et al. | 427/126.3 |

FOREIGN PATENT DOCUMENTS 0 810 430  12/1997  European Pat. Off. .

Primary Examiner—T. Tung
Attorney, Agent, or Firm—Sughrue, Mion, Zinn, Macpeak & Seas, PLLC

[57] ABSTRACT

There is described a gas-component concentration sensor, a method of using the sensor, and a method of manufacturing a particular electrode of the sensor, wherein the sensor comprises:

a first measurement chamber, an oxygen partial-pressure detection electrode in the first measurement chamber, a first oxygen-ion pump cell within and outside the first measurement such that in response to a voltage applied between the pair electrodes the cell pumps out oxygen to an extent such that a gas component such as $NO_x$ partially decomposes in said first measurement chamber in an amount of not more than 40 wt. % of the gas component present;

a second measurement chamber into which the measurement gas is introduced from the first measurement chamber, a second oxygen pump cell having a pair of electrodes such that in response to a voltage applied therebetween the second oxygen-ion pump cell decomposes the gas component within the second measurement chamber;

wherein the pair of electrodes of the first oxygen ion pump cell the electrode provided inside first measurement chamber includes fine particles having a function of suppressing dissociation of the gas component that are formed on and carried by a first constituent component of the electrode.

2 Claims, 5 Drawing Sheets

METHOD FOR MANUFACTURING ELECTRODE

BACKGROUND OF THE INVENTION

1. Field of the Invention

The present invention generally relates to an electrode of an oxygen-ion conductive cell used in sensors for detecting gas components such as $NO_x$, $CO_2$, $SO_x$, HC and $H_2O$, such as a $NO_x$—concentration sensor used for detecting the concentration of nitrogen oxides contained, e.g., in an exhaust gas from a stationary internal combustion engine for industrial use or an internal combustion engine for an automobile, ship, or airplane, or a combustion gas of a boiler or the like. More particularly, the present invention relates to an electrode provided in a first measurement chamber among a pair of electrodes of a first oxygen-ion pump cell of the sensor for measuring $NO_x$ concentration, to a method of measuring $NO_x$-concentration using said sensor, and to a method for manufacturing the electrode provide in the first measurement chamber of the sensor.

2. Description of Related Art

In order to cope with increasingly strict regulation of exhaust gas, there has been studied a technique for directly measuring gas components in exhaust gas from an engine in order to control the engine or a catalyst device. Especially, because of the capability of measuring $NO_x$ concentration without influence of interference gases such as HC and CO, there has been widely studied an $NO_x$-concentration sensor which utilizes an oxygen-ion conductor such as $ZrO_2$ and in which oxygen is pumped out through a first oxygen-ion pump cell to such an extent that $NO_x$ substantially does not decompose, $NO_x$ contained in the remaining gas is decomposed through use of a second oxygen-ion pump cell, and the decomposition of the $NO_x$ is detected in the form of current.

For example, Japanese Patent Application Laid-Open No. 8-271476 which corresponds to U.S. Pat. No. 5,672,811 discloses a method of measuring a gas component and a sensing device for measuring the gas component. In this device, the electrode that constitutes the first oxygen pump means and is disposed within the first space is a cermet electrode formed of a mixture of Pt and $ZrO_2$ or a cermet electrode formed of a Pt/Au alloy. The method of forming the Pt/Au-alloy cermet electrode or the microstructure of the cermet is not described in this prior art. However, it is supposedly generally formed as follows. That is, Pt powder, Au powder, $ZrO_2$ powder, and a proper amount of organic solvent may be mixed and dispersed to obtain a mixture, to which may be added an organic binder. Subsequently, a viscosity modifier may be further added to and mixed with the mixture to obtain paste. The paste may be then applied onto a solid electrolyte layer and baked. As shown in FIG. 2, the thus-supposedly formed electrode will have a texture such that precious-metal alloy particles and $ZrO_2$ particles exist independently of each other.

In the case of $NO_x$ measurement, the above-described first oxygen pumping means has a function of selectively pumping out oxygen without dissociating $NO_x$. However, when the method of simply adding Au powder to an electrode constituent component is employed, Au and Pt do not form an alloy if the ratio of Au exceeds a certain value, so that Au unevenly disperses within the electrode (see FIG. 2). In such a case, the function of suppressing $NO_x$ dissociation unstably varies with time and also varies locally, and therefore, the function of suppressing $NO_x$ dissociation is difficult to improve. Further, since the function of the Au component for suppressing $NO_x$ dissociation is unstable, the oxygen concentration within the first internal space must be set slightly higher than a theoretical level, in consideration of variation in the suppressing function (because $NO_x$ dissociates when the oxygen concentration decreases). The excessive oxygen causes an error when a very small $NO_x$ concentration is measured.

In view of the foregoing, an object of the present invention is to provide an electrode which is provided in a first measurement chamber of a $NO_x$-concentration sensor as one of the paired electrodes of a first oxygen-ion pump cell, which has an enhanced function of suppressing $NO_x$ dissociation, and which stably provides the function of suppressing $NO_x$ dissociation.

SUMMARY OF THE INVENTION

The present inventors have found that when particles (electrode constituent component) formed of an inorganic metallic oxide that carries Au and/or Cu and serves as an oxygen-ion conductor are used as the constituent components of the electrode which is provided in a first measurement chamber of, e.g., a $NO_x$-concentration sensor as one of the paired electrodes of a first oxygen-ion pump cell, the above-described suppressing function is enhanced and stabilized over a wide range of Au content from a very low Au content to a very high Au content. Based on this finding, the inventors conducted further studies, and have now completed the present invention.

To achieve the above object, the present invention provides an $NO_x$-concentration sensor comprising: a first measurement chamber into which a measurement gas is introduced via a first diffusion resistor; an oxygen partial-pressure detection electrode for measuring a partial pressure of oxygen contained in the measurement gas within the first measurement chamber; a first oxygen-ion pump cell having a pair of electrodes provided within and outside the first measurement chamber, such that in response to a voltage applied between the pair of electrodes based on the electrical potential of the oxygen partial-pressure detection electrode, the first oxygen-ion pump cell pumps out oxygen within the measurement gas from the first measurement chamber to an extent such that $NO_x$ partially decomposes in the first measurement chamber, in an amount of not more than 40 wt. % of the $NO_x$ present; a second measurement chamber into which the measurement gas is introduced from the first measurement chamber via a second diffusion resistor; and a second oxygen-ion pump cell having a pair of electrodes, one of which is provided inside the second measurement chamber, such that in response to a voltage applied between the pair of electrodes, the second oxygen-ion pump cell decomposes $NO_x$ within the second measurement chamber and pumps out the dissociated oxygen, so that a current corresponding to an $NO_x$ concentration flows through the second oxygen-ion pump cell. Among the pair of electrodes of the first oxygen-ion pump cell, the electrode provided inside the first measurement chamber includes fine particles that are carried by a component of the electrode and that are formed of a first constituent component having a function of suppressing $NO_x$ dissociation.

In a preferred embodiment, from 0.1 wt. % to 43 wt. % of the $NO_x$ decomposes. In a more preferred embodiment, from 1 wt. % to 30 wt. % of $NO_x$ decomposes. In a still more preferred embodiment from 2 wt. % to 20 wt. % of the $NO_x$ decomposes.

In another aspect of the invention, the $NO_x$-concentration sensor is used in the manner indicated in the foregoing description to measure the $NO_x$-concentration in an exhaust gas.

The present invention also provides a method of manufacturing an electrode of a gas sensor, the method comprising the steps of impregnating, as a first constituent component, a solution containing one or more elements selected from the group consisting of Au and Cu into solid electrolyte powder having oxygen-ion conductivity; drying and firing the solid electrolyte powder in order to obtain first-constituent-component carrying powder in which fine particles formed of the first constituent component are carried on the solid electrolyte powder; mixing the first-constituent-component carrying powder with powder of one or more kinds of precious metal components selected from the group consisting of Pt, Pd, Rh, Ir and Re; preparing paste from the resultant mixed powder; applying the paste onto a surface of a compact that becomes, after firing, a solid electrolyte layer constituting the first oxygen-ion pump cell; and firing the paste in order to form the electrode.

DETAILED DESCRIPTION OF THE INVENTION

Figure 1:
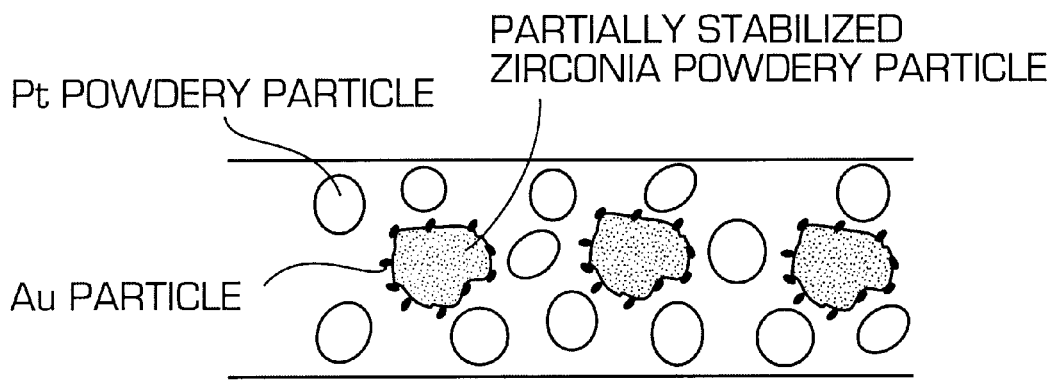
FIG. 1 is a schematic view for describing the texture of an electrode according to an embodiment of the present invention.

A preferred embodiment of the present invention will now be described. First, a description is given of a material for forming an electrode provided in a first measurement chamber of an $NO_x$-concentration sensor as one of paired electrodes of a first oxygen-ion pump cell thereof.

That is, in the electrode provided in the first measurement chamber as one of the paired electrodes of the first oxygen-ion pump cell, a first constituent component having a function of suppressing $NO_x$ dissociation preferably has a function of catalyzing oxygen dissociation. Further, in the electrode, Pt, Pd, or Rh having a strong function of catalyzing oxygen dissociation is preferably used, solely or in combination, as a second constituent component. Although the second constituent component has a function of dissociating $NO_x$, the function of dissociating $NO_x$ is suppressed by means of the first constituent component. When the first constituent component is Au, the electrode preferably contains the first constituent component in an amount of 0.01 wt. % or more in order to obtain a sufficient function of suppressing $NO_x$ dissociation. Further, since Au is finely and uniformly dispersed throughout the electrode, a sufficient and stable function of suppressing $NO_x$ dissociation is obtained even when the Au content of the electrode is made 50% or less (based on weight). The first constituent component may be carried such that the first constituent component adheres to the surface of particles of the electrode constituent component, or such that fine particles formed of the first constituent component such as Au exist within fine pores of the particles. Particles of an electrode constituent component (e.g., solid electrolyte particles) on which fine particles of the first constituent component are carried are preferably larger than the fine particles. Further, as will be described later, particles of the electrode constituent component which carry fine particles of the first constituent component are formed of the same solid electrolyte as an oxygen-ion-conductive solid electrolyte that constitutes the first oxygen-ion pump cell from the viewpoint of prevention of separation of the electrode during drying, during firing, or after firing, as well as easiness of integral firing. The ratio of the diameter of particles of the electrode constituent component which carry fine particles of the first constituent component to the diameter of the fine particles of the first constituent component is preferably 50–50,000 and more preferably 500–5,000.

As the first constituent component, there is preferably used one or more elements selected from the group consisting of Au and Cu. As the second constituent component, there is preferably used one or more elements selected from the group consisting of Pt, Pd, and Rh. As the electrode constituent component which carries fine particles of the first constituent component, there are preferably used particles of an inorganic metallic oxide, especially, $ZrO_2$, which has an oxygen-ion conductivity and which has good conformity with the solid electrolyte that constitutes the sensor. Alternatively, as the oxygen-ion-conductive particles of an inorganic metallic oxide there may be used $ZrO_2$ powder, $CeO_2$ powder, $HfO_2$ powder, or $ThO_2$ powder, which is partially or completely stabilized. Also, a mixture of partially stabilized powder and completely stabilized powder may be used. One or more kinds of rare earth oxides of CaO, MgO, or $Y_2O_3$ (e.g., $La_2O_3$ and $Gd_2O_3$) may be used as the stabilizer for partial or complete stabilization. Preferably, yttrium-partially-stabilized $ZrO_2$ powder (i.e., $ZrO_2$ powder partially stabilized through use of yttrium) is used. $ZrO_2$ serving as a base material may contain hafnia. Other types of stabilizers or other types of solid electrolytes may be used. In addition, there is preferably used the same material as that used for the oxygen-ion-conductive solid electrolyte layer serving as a base material.

The electrode provided in the first measurement chamber as one of paired electrodes of the first oxygen-ion pump cell may be formed such that, in at least a portion including a surface intended for contact with exhaust gas, the first constituent component having a function of suppressing the dissociation of $NO_x$ exists in a larger amount as compared with the remaining portion. Further, the electrode may be such that the electrode itself is formed of the second constituent component having a strong oxygen dissociation function, and a layer containing a large amount of the first constituent component is formed on the surface thereof.

Furthermore, Au and/or Cu or the like may be added in order to decrease the catalytic activity of, e.g., Pt. Moreover, a metallic coating layer containing Au or Ag as a main component or a coating layer of oxide such as $SnO_2$, ZnO, $In_2O_3$, $WO_3$, $Bi_2O_3$ may be applied on the surface of the electrode.

An electrode comprising oxygen-ion conductive oxide particles (e.g., $ZrO_2$) and oxygen-dissociating catalytic metal particles (e.g., Pt), but without the fine metal particles having a function of suppressing dissociation of the gas component in the first measurement chamber in accordance with this invention is quite undesirable, and would result in a $NO_x$ decomposition of more than 60 wt. % at a sensor first measurement chamber temperature between 700 and 850° C. and under an oxygen partial pressure of less than $10^{-6}$ atm.

For an electrode intended for use in a first measurement chamber temperature of 700 to 850° C. and under an oxygen partial pressure of less than $10^{-6}$ atm., the composition thereof is preferably 75–92 wt. % Pt. 7–25 wt. % $ZrO_2$, and Au (or Cu or an alloy thereof) in an amount of 0.1–5 wt. %.

Next, a description is given of a preferred process of manufacturing the above-described electrode. Au solution (e.g., solution of gold chloride acid) is impregnated into an oxygen-ion-conductive powder, which is then dried and fired in order to cause Au to adhere onto the powder, thereby yielding Au-carrying powder. The Au-carrying powder and Pt powder are mixed together, and a binder, an organic solvent, and a viscosity modifier are added thereto in proper amounts in order to obtain paste. The paste is then applied, through use of screen printing or the like, onto a green sheet that becomes an oxygen-ion-conductive solid electrolyte layer (a solid electrolyte layer constituting the first oxygen-ion pump cell). Subsequently, other green sheets are superposed, and all the superposed green sheets are dried and fired, so that the above-described electrode is formed on the first oxygen-ion pump cell and in the first measurement chamber.

Figure 2:
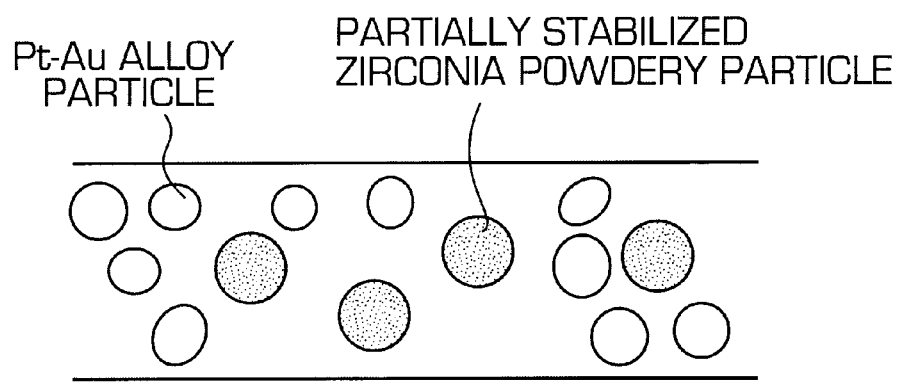
FIG. 2 is a schematic view for describing the texture of an electrode according to a comparative example.

The texture of the thus-manufactured electrode is compared with the texture of a conventional electrode (which is obtained through mixing precious metal powder and oxygen-conductive inorganic powder, followed by firing). FIG. 1 is a schematic view for describing the texture of an electrode according to the embodiment of the present invention, while FIG. 2 is a schematic view for describing the texture of an electrode according to a conventional electrode, which serves as a comparative example. In the electrode texture show in FIG. 1, Au fine particles are carried on particles (of the main constituent component of the electrode) which are larger than the Au fine particles, and therefore the Au component finely disperses. In the electrode texture shown in FIG. 2, if particles of Pt-Au alloy exist in uneven concentrations, the Au component comes to exist in locally uneven concentrations. Accordingly, the electrode shown in FIG. 2 has the following drawback that when a single element is considered, the function of suppressing $NO_x$ dissociation varies locally. When elements are manufactured in a plurality of lots, the function of suppressing $NO_x$ dissociation will vary greatly between the lots. Therefore, the oxygen concentration within the first measurement chamber, which must be set as low as possible, cannot be made as low as desired.

Next is described the reason why the oxygen concentration within the first measurement chamber is set to a low level. First, a description will be given of the principle of measurement of the $NO_x$-concentration sensor according to the embodiment of the present invention.

(1) Exhaust gas flows into the first measurement chamber via a first diffusion hole having a diffusion resistance.

(2) By means of the first oxygen-ion pump cell, oxygen within the first measurement chamber is pumped out to a degree such that $NO_x$ substantially does not decompose or does partially decompose in an amount of not more than 40 wt. % (the oxygen partial pressure in the first measurement chamber is controlled in accordance with a signal output from the oxygen partial-pressure detection electrode).

(3) Gas ($O_2$ gas having a controlled concentration +$NO_x$ gas) in the first measurement chamber flows into the second measurement chamber via a second diffusion hole having a diffusion resistance.

(4) $NO_x$ gas in the second measurement chamber is decomposed into $N_2$ gas and $O_2$ gas as oxygen is further pumped out by means of the second oxygen-ion pump cell.

(5) Since there exists a linear relationship between the $NO_x$ concentration and the second oxygen pump current $I_{P2}$ flowing through the second oxygen-ion pump cell, the $NO_x$ concentration can be detected through the detection of $I_{p2}$.

As described above, the $NO_x$ concentration is detected based on the amount of oxygen ions dissociated as a result of decomposition of $NO_x$ in the second measurement chamber. Therefore, the concentration of oxygen defusing and flowing into the second measurement chamber must be made constant or zero. Further, if the oxygen concentration is high, the second oxygen pump current $I_{P2}$ is affected by temperature and by other gas components, resulting in an increased error. Therefore, oxygen must be pumped out as much as possible from the measurement gas which diffuses and flows into the first measurement chamber to an extent such that $NO_x$ partially decomposes in the first measurement chamber, in an amount of not more than 40 wt. % of the $NO_x$ present though.

EXAMPLE

An example of the present invention will be described with reference to the drawings. First, with reference to FIG. 3, a description will be given of the structure of an $NO_x$-concentration sensor according to the example of the present invention. The sensor shown in FIG. 3 includes four solid electrolyte layers 5-1, 5-2, 5-3, and 5-4 superposed in this sequence, and insulating layers 11-1, 11-2, and 11-3 are interposed between the solid electrolyte layers 5-1, 5-2, 5-3, and 5-4. The sensor further includes a first oxygen-ion pump cell 6, an oxygen concentration measurement cell 7, and a second oxygen-ion pump cell 8. The first oxygen-ion pump cell 6 has a pair of electrodes 6a and 6b provided on opposite sides of the solid electrolyte layer 5-1. The electrode 6a of the first oxygen-ion pump cell 6 is located outside the first measurement chamber 2. The electrode 6b of the first oxygen-ion pump cell 6 is located within the first measurement chamber 2. The oxygen concentration measurement cell 7 has a pair of oxygen-partial-pressure detection electrodes 7a and 7b provided on opposite sides of the solid electrolyte layer 5-2. The second oxygen-ion pump cell 8 has a pair of electrodes 8a and 8b provided on the upper surface of the solid electrolyte layer 5-4. The electrode 8a of the second oxygen-ion pump cell 8 is located within the second measurement chamber 4. The electrode 8b of the second oxygen-ion pump cell 8 is located outside the second measurement chamber 4. The electrode 6b of the first oxygen-ion pump cell 6 located within the first measurement chamber 2 has a texture as shown in FIG. 1, in which Au fine particles are carried on partially stabilized $ZrO_2$ powder, and the Au-carrying partially-stabilized $ZrO_2$ powder and Pt particles constitute the electrode 6b. Between the first oxygen-ion pump cell 6 and the oxygen concentration measurement cell 7 is provided the first measurement chamber 2 which is defined by the insulating layer 11-1 and the upper and lower solid electrolyte layers 5-1 and 5-2. Similarly, on the second oxygen-ion pump cell 8 is provided the second measurement chamber 4 which is defined by the insulating layer 11-3 and the solid electrolyte layers 5-3 and 5-4. Further, at one end of the first measurement chamber 2, first diffusion holes 1 are provided at opposite sides in the lateral direction of the sensor (in the direction perpendicular to the sheet of FIG. 3), and at the other end of the first measurement chamber 2 the opening of a second diffusion hole 3 is provided separately from the first diffusion hole 1. The second diffusion hole 3 penetrates the oxygen concentration measurement cell 7 and the solid electrolyte layer 5-3 in order to connect the first measurement chamber 2 and the second measurement chamber 4.

In the sensor, the electrodes 8a and 8b formed of porous alloy (e.g., Pt, Rh alloy) are both provided on the same surface of the solid electrolyte layer 5-4 that constitutes the second oxygen-ion pump 8. Although the electrodes 8a and 8b are separated from each other by means of the insulating layer 11-3, oxygen ions move through the solid electrolyte layer 5-4, so that current $I_{P_2}$ flows accordingly. Direct contact between the electrode 8b and the atmosphere outside the sensor is prevented by means of the solid electrolyte layer 5-4, the insulating layer 11-3, and the lead portion 8d. Further, the porous lead portion 8d having a diffusion resistance allows oxygen pumped out by means of the second oxygen-ion pump cell 8 to escape through the lead portion 8d. Further, lead portions (wires) 8c and 8d are electrically connected to the electrodes 8a and 8b. Among them, the lead portion 8d connected to the electrode 8b outside the second measuring chamber 4 is made porous in order to allow diffusion of oxygen ions. Accordingly, oxygen decomposed from $NO_x$ gas by means of the second oxygen-ion pump cell 8 and pumped from the electrode 8a to the electrode 8b is discharged via the lead portion 8d.

Figure 3:
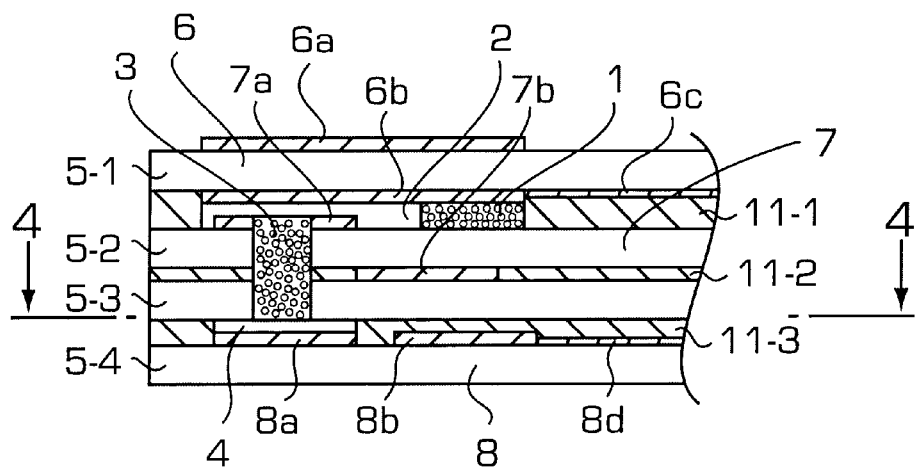
FIG. 3 is a longitudinal cross section of an $NO_x$-concentration sensor according to the first embodiment of the present invention, showing the structure of the sensor.
Figure 4:
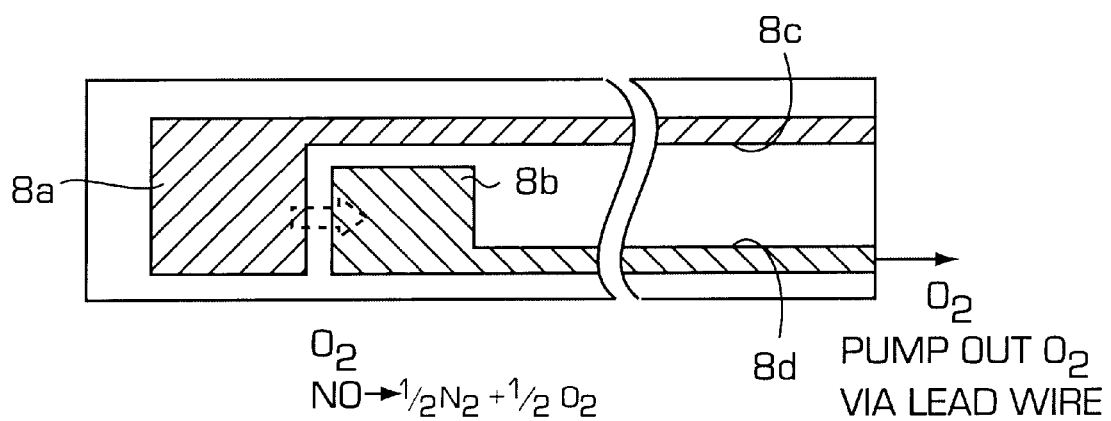
FIG. 4 is a horizontal sectional view taken along line A–B in FIG. 3.

FIG. 4 is a horizontal cross-sectional view showing the shape of the porous electrodes 8a and 8b of the $NO_x$-concentration sensor (corresponding to a horizontal cross-sectional view taken along line A–B in FIG. 3). As is apparent from FIG. 4, the lead portion 8d is in contact with the atmosphere outside the sensor (atmospheric air or measurement gas), and serves to connect the electrode 8b to the outside atmosphere via the diffusion resistor.

The principle of measurement of the sensor shown in FIG. 3 has been described above. When measurement gas diffuses into the first diffusion hole 1 to enter the first measurement chamber 2, an electromotive force corresponding to the oxygen concentration of the measurement gas in the first measurement chamber 2 is generated across the paired electrodes 7a and 7b of the oxygen concentration measurement cell 7. The voltage applied to the first oxygen-ion pump cell 6 is controlled such that the voltage induced by the electromotive force becomes constant, e.g., at 450 mV (digital control may be performed through use of a microcomputer, or analog control may be performed). Among the paired electrodes 6a and 6b of the first oxygen-ion pump cell 6, the electrode 6b—which is provided within the first measurement chamber 2 and in which Au fine particles are carried on partially stabilized $ZrO_2$ powder—suppresses $NO_x$ dissociation. In such a state, excessive oxygen is pumped out by means of the first oxygen-ion pump cell 6, so that measurement gas having a constant oxygen concentration diffuses into the second measurement chamber 4 via the second diffusion hole 3. Since a voltage is applied between the paired electrodes 8a and 8b of the second oxygen-ion pump cell 8, the residual oxygen is pumped out. Further, due to catalytic action of the electrode formed of Pt alloy or Rh alloy, $NO_x$ is decomposed into $N_2$ and $O_2$. The $O_2$ becomes oxygen ions, which move through the solid electrolyte layer of the second oxygen-ion pump cell 8. As a result, a second oxygen pump current $IP_2$ corresponding to the amount of decomposed $NO_x$ flows between the paired electrodes 8a and 8b of the second oxygen-ion pump cell 8. The $NO_x$ concentration can be measured through measurement of the current $IP_2$.

In this sensor, the electrode 8b—which serves as a counterpart electrode of the electrode 8a of the second oxygen-ion pump cell 8 within the second measurement chamber 4—is disposed within the element (between the superposed solid electrolyte layers). Therefore, the solid electrolyte layer 5-4 and the insulating layer 11-3 serve as protection means for the electrode 8b. In addition, the lead portion 8d serves as diffusion resistor means. Thus, the electrode 8b is isolated from the atmosphere of measurement gas (exhaust gas) and thus prevented from coming into direct contact with the outside atmosphere. Further, since pumped-out oxygen is pooled around the electrode 8b, the oxygen concentration around (in the vicinity of) the electrode 8b is stabilized, resulting in stable generation of the electromotive force between the paired electrodes 8a and 8b of the second oxygen-ion pump cell 8. Moreover, since the generated electromotive force is stabilized, the effective pump voltage ($V_{P2}$ - the electromotive force) of the pump voltage $V_{P2}$ applied to the second oxygen-ion pump cell 8 is stabilized, resulting in a reduction in the degree of dependency of the $NO_x$ concentration measurement on oxygen concentration.

Example of Manufacture

Figure 5:
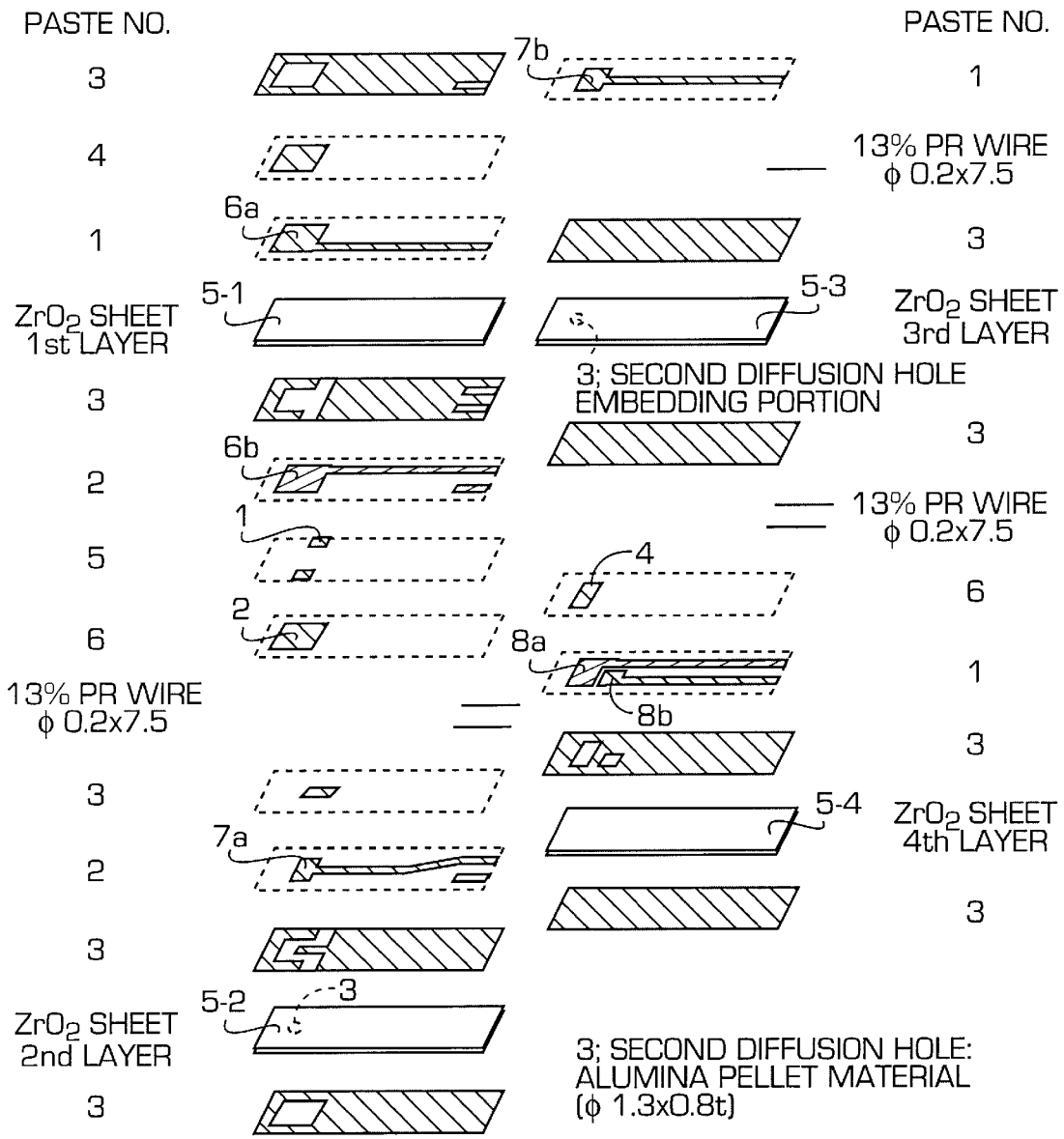
FIG. 5 is a view showing a method of manufacturing an $NO_x$-concentration sensor used in a measurement and the layout thereof.

FIG. 5 shows the layout of the $NO_x$ concentration sensor according to the example of the present invention shown in FIG. 3. $ZrO_2$ green sheets, electrode paste, and the like are superposed in the sequence from the upper left to the lower left and then from the upper right to the lower right of FIG. 5, and then subjected to drying and firing in order to manufacture an integrated sensor. Paste materials for insulating coats, electrodes, and the like are formed on corresponding $ZrO_2$ green sheets in a superposed manner through screen printing. Next, a description will be given of an example of manufacture of the respective components, such as $ZrO_2$ green sheets.

Formation of $ZrO_2$ Green Sheets (First Through Fourth Layers)

$ZrO_2$ powder was calcined at 600° C. in an atmospheric furnace for 2 hours. Calcined $ZrO_2$ powder (30 kg), a dispersing agent (150 g), and an organic solvent (10 kg) were charged into a trommel together with grinding balls (60 kg) and were mixed for about 50 hours in order to disperse the $ZrO_2$ powder into the organic solvent. Further, an organic solvent (10 kg) into which an organic binder (4 kg) had been dissolved was added to the mixture, which was then mixed for 20 hours to obtain slurry having a viscosity of about 10 Pa·s. A $ZrO_2$ green sheet having a thickness of about 0.4 mm was prepared from the slurry in accordance with a doctor blade method, and then dried at 100° C. for 1 hour.

Paste for Printing (1) For the oxygen-partial-pressure detection electrode (oxygen reference electrode) 7a: Pt powder (19.8 g), $ZrO_2$ powder (2.8 g), Au powder (0.2 g), and a proper amount of an organic solvent were placed into a crusher (or a pot mill) and mixed for 4 hours for dispersion. Further, an organic solvent (20 g) into which an organic binder (2 g) had been dissolved was added to the mixture, to which was further added a viscosity modifier (5 g), and thereafter mixing was performed for 4 hours. Thus, paste having a viscosity of about 150 Pa·s was prepared.

(2) For the first oxygen-ion pump electrode 6a, the oxygen-partial-pressure detection electrode (oxygen reference electrode) 7b, and the second oxygen-ion pump electrodes 8a and 8b: Pt powder (20 g), $ZrO_2$ powder (2.8 g), and a proper amount of an organic solvent were placed into a crusher (or a pot mill) and mixed for 4 hours for dispersion. Further, an organic solvent (20 g) into which an organic binder (2 g) had been dissolved was added to the mixture, to which was further added a viscosity modifier (5 g), and thereafter mixing was performed for 4 hours. Thus, paste having a viscosity of about 150 Pa·s was prepared.

(2') For the first oxygen-ion pump electrode 6b: A description will be given of the material of the electrode 6b provided in the first measurement chamber 2, among the paired electrodes 6a and 6b of the first oxygen-ion pump 6. $ZrO_2$ powder partially stabilized through use of yttrium (hereinafter referred to as "partially stabilized $ZrO_2$ powder") was used as a powder material of an oxygen-ion-conductive solid electrolyte that carries Au, which is the first constituent component of the electrode 6b. Partially stabilized $ZrO_2$ powder (2.8 g, particle size: 0.1–50 μm) was impregnated with a solution of gold chloride acid (1.83 g, Au content: 30.52 wt. %), and was then dried at 120° C. for 7 hours and fired at 800° C. for 3 hours. Thus, there was obtained powder material (3.36 g) in which Au fine particles (particle size: 1 μm or less) were carried on partially stabilized $ZrO_2$ powder. Paste containing the powder material was prepared as follows. The powder material (3.36 g) in which Au fine particles were carried on partially stabilized $ZrO_2$ powder was crushed for 12 hours through use of a crusher, mixed with porous powder of Pt (20 g, particle size: 1–50 μm) and a proper amount of an organic solvent, and then subjected to crushing for 4 hours by use of a crusher (or pot mill). Subsequently, an organic solvent (20 g) into which an organic binder (2 g) had been dissolved was added to the mixture, to which was further added a viscosity modifier (5 g), and thereafter mixing was performed for 4 hours. Thus, paste having a viscosity of about 140 Pa·s was prepared.

(3) For the insulating and protective coats: Alumina powder (50 g) and a proper amount of an organic solvent were placed into a crusher (or a pot mill) and mixed for 12 hours for dissolution. Further, a viscosity modifier (20 g) was added, and thereafter mixing was performed for 3 hours. Thus, paste having a viscosity of about 100 Pa·s was prepared.

(4) For Pt-containing porous material (for lead wires): Alumina powder (10 g), Pt powder (1.5 g), an organic binder (2.5 g), and an organic solvent (20 g) were placed into a crusher (or a pot mill) and mixed for 4 hours. Further, a viscosity modifier (10 g) was added, and mixing was performed for 4 hours. Thus, paste having a viscosity of about 100 Pa·s was prepared.

(5) For the first diffusion hole: Alumina powder (10 g, average particle size: about 2 μm), an organic binder (2 g), and an organic solvent (20 g) were placed into a crusher (or a pot mill) and mixed for dispersion. Further, a viscosity modifier (10 g) was added, and thereafter mixing was performed for 4 hours. Thus, paste having a viscosity of about 400 Pa·s was prepared.

(6) For the carbon coat: Carbon powder (4 g) and an organic solvent (40 g) were placed into a crusher (or a pot mill) and mixed for 4 hours for dispersion. Further, a viscosity modifier (5 g) was added, and thereafter mixing was performed for 4 hours to prepare the paste. In an example application, formation of a carbon coat through printing prevents contact between the first oxygen-ion pump electrode 6b and the oxygen reference electrode 7a. The carbon coat is also used to form the first and second measurement chambers. Since carbon burns and disappears during firing, the carbon coat layers do not exist in the fired body.

Pellet Material (7) For the second diffusion hole: Alumina powder (20 g, average particle size: several μm), an organic binder (8 g), and an organic solvent (20 g) were placed into a crusher (or a pot mill), mixed for 1 hour, and then granulated. Subsequently, a pressure of about 2 tons/cm$^2$ was applied to the granulated mixture through use of a die press in order to prepare a cylindrical press-formed body (a green body) having a diameter of 1.3 mm and a thickness of 0.8 mm. The green body was inserted into predetermined holes of the $ZrO_2$ green sheets of the second and third layers, which were then pressure-bonded for integration and fired in order to form the second diffusion hole in the sensor.

Method of Superposing $ZrO_2$ Layers

After the second and third layers were press-bonded, the portion (diameter: 1.3 mm) where the second diffusion hole penetrates was punched, and the cylindrical green body serving as the second diffusion hole was embedded in the punched portion. Subsequently, the first through fourth $ZrO_2$ green sheets were pressure-bonded at a pressure of 5 kg/cm$^2$ for 1 minute.

Binder Burn-out and Firing

The press-bonded green body was subjected to a binder burn-out process at 400° C. for 2 hours, and then fired at 1500° C. for 1 hour.

Next, the characteristics of the sensor according to the example of the present invention having the structure shown in FIG. 3 and manufactured in accordance with the above-described exemplary manufacturing process were investigated. A measurement gas was fed into the sensor, and corresponding voltages were applied to the paired electrodes 6a and 6b of the first oxygen-ion pump cell 6 and to the paired electrodes 8a and 8b of the second oxygen-ion pump cell 8. Then, there were measured the first oxygen pump current flowing through the first oxygen-ion pump cell 6 and the second oxygen pump current flowing through the second oxygen-ion pump cell 8. In FIGS. 6–9, black square dots show the data obtained from the Example.

Separately, sensors were manufactured as Comparative Examples 1–4 while the material of the electrode was changed. The characteristics of the sensors were investigated in the same manner as in the Example. Since the sensors of Comparative Examples 1–4 were manufactured in the same manner as in the Example except for the electrode of the first oxygen-ion pump cell disposed within the first measurement chamber, only the process for manufacturing the electrode will be described. For Comparative Example 1 (shown by black circular dots in FIGS. 6–9), the electrode of the first oxygen-ion pump cell disposed within the first measurement chamber was manufactured such that the electrode contained 5 wt. % of Ir. Pt powder (19.0 g), $ZrO_2$ powder (2.8 g), Ir powder (1.0 g) and a proper amount of an organic solvent were placed into a crusher (or a pot mill) and mixed for 4 hours for dispersion. Further, an organic solvent (20 g) into which an organic binder (2 g) had been dissolved was added to the mixture, to which was further added a viscosity modifier (5 g), and thereafter mixing was performed for 4 hours. Thus, paste having a viscosity of about 140 Pa·s was prepared. Subsequently, in the same manner as in the Example, the paste was printed, dried, and fired. The thus-obtained electrode had a texture identical with that shown in FIG. 2, wherein Pt particles, Ir particles, and alloy particles thereof exist in a dispersed manner. Ir and Pt have the same level of $NO_x$ dissociation function.

For Comparative Example 2 (shown by black triangular dots in FIGS. 6–9), the electrode of the first oxygen-ion pump cell disposed within the first measurement chamber was manufactured such that the electrode contained 1 wt. % of Ir. Pt powder (19.8 g), $ZrO_2$ powder (2.8 g), Ir powder (0.2 g) and a proper amount of an organic solvent were placed into a crusher (or a pot mill) and mixed for 4 hours for dispersion. Further, an organic solvent (20 g) into which an organic binder (2 g) had been dissolved was added to the mixture, to which was further added a viscosity modifier (5 g), and thereafter mixing was performed for 4 hours. Thus, paste having a viscosity of about 140 Pa·s was prepared. Subsequently, in the same manner as that for the Example, the paste was printed, dried, and fired. The thus-obtained electrode has a texture identical with that shown in FIG. 2, wherein Pt particles, Ir particles, and alloy particles thereof exist in a dispersed manner.

For Comparative Example 3 (shown by black diamond-shaped dots in FIGS. 6–9), the electrode of the first oxygen-ion pump cell disposed within the first measurement chamber was manufactured in the same manner as in the Example, except that Pd was used in place of Au, and Pd was carried on partially stabilized $ZrO_2$ powder such that the Pd content of the electrode became 2.4 wt. %. That is, in order to obtain an electrode in which Pd is carried on oxygen-ion conductive solid electrolyte powder, $ZrO_2$ powder (2.8 g) partially stabilized through use of yttria was impregnated with solution of palladium nitrate (12.76 g, Pd content: 4.390%), and was then dried at 120° C. for 7 hours and fired at 800° C. for 3 hours Thus, there was obtained powder material (5.6 g) in which Pd fine particles were carried on partially stabilized $ZrO_2$ powder. The powder material in which Pd fine particles were carried on partially stabilized $ZrO_2$ powder was crushed for 12 hours through use of a crusher, mixed with porous powder of Pt (20 g) and a proper amount of an organic solvent, and then crushed for 4 hours by use of a crusher (or pot mill). Subsequently, an organic solvent (20 g) into which a binder (2 g) had been dissolved was added to the mixture, to which was further added a viscosity modifier (5 g), and thereafter mixing was performed for 4 hours. Thus, paste having a viscosity of about 140 Pa·s was prepared. The paste was screen-printed on a partially stabilized $ZrO_2$ sheet, which was then subjected to a binder burn-out process and fired at 1500° C. for 1 hour in order to obtain the electrode.

For Comparative Example 4 (EP shown by white square dots in FIGS. 6 and 7), the electrode of the first oxygen-ion pump cell disposed within the first measurement chamber was a conventional Pt electrode prepared in the following manner. Pt powder (20.0 g), $ZrO_2$ powder (2.8 g), and a proper amount of an organic solvent were placed into a crusher (or a pot mill) and mixed for 4 hours for dispersion. Further, an organic solvent (20 g) into which an organic binder (2 g) had been dissolved was added to the mixture, to which was further added a viscosity modifier (5 g), and mixing was performed for 4 hours. Thus, paste having a viscosity of about 140 Pa·s was prepared. Subsequent processes were performed in the same manner as those for the Example to complete the electrode. The thus-obtained electrode had a texture similar to that shown in FIG. 2.

For Comparative Example 5 (UP shown by white square dots in FIGS. 8 and 9), the electrode of the first oxygen-ion pump cell disposed within the first measurement chamber was manufactured from a material obtained by mixing Au powder into paste (which Au was not carried on the powdery material). That is, Pt powder (19.8 g), $ZrO_2$ powder (2.8 g), Au (0.2 g), and a proper amount of an organic solvent were placed into a crusher (or a pot mill) and mixed for 4 hours for dispersion. Further, an organic solvent (20 g) into which an organic binder (2 g) had been dissolved was added to the mixture, to which was further added a viscosity modifier (5 g), and thereafter mixing was performed for 4 hours. Thus, paste having a viscosity of about 140 Pa·s was prepared. Subsequently, in the same manner as for the Example, printing was performed through use of the paste.

Figure 6:
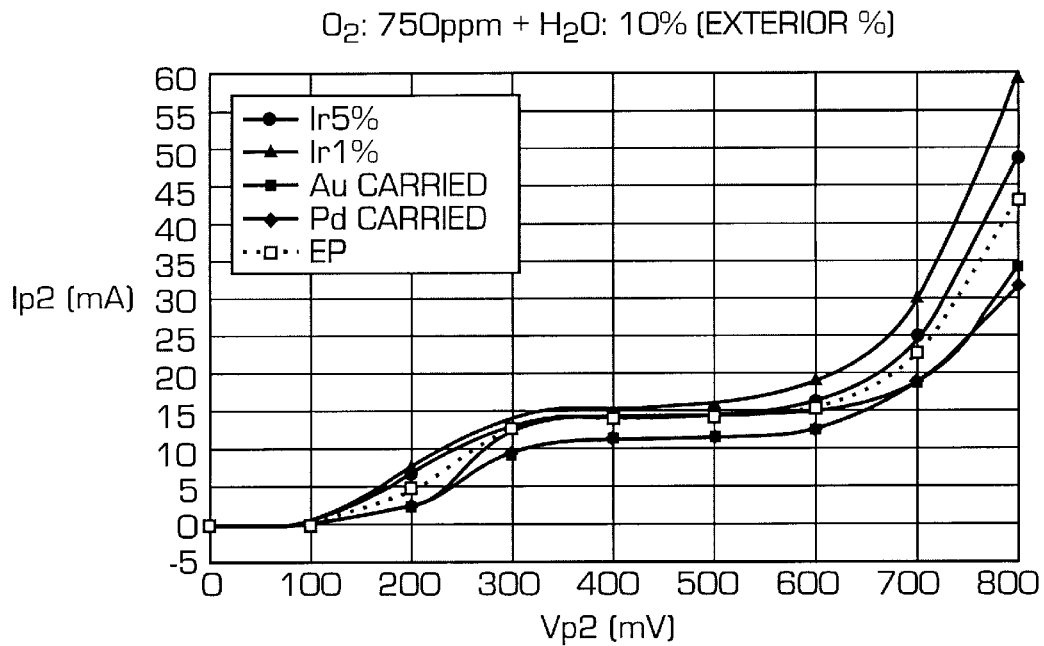
FIG. 6 is a graph showing the current characteristic of the second oxygen pump of each of the sensors according to an Example and Comparative Examples 1–4 (measurement gas containing 750 ppm of $O_2$ is introduced).
Figure 7:
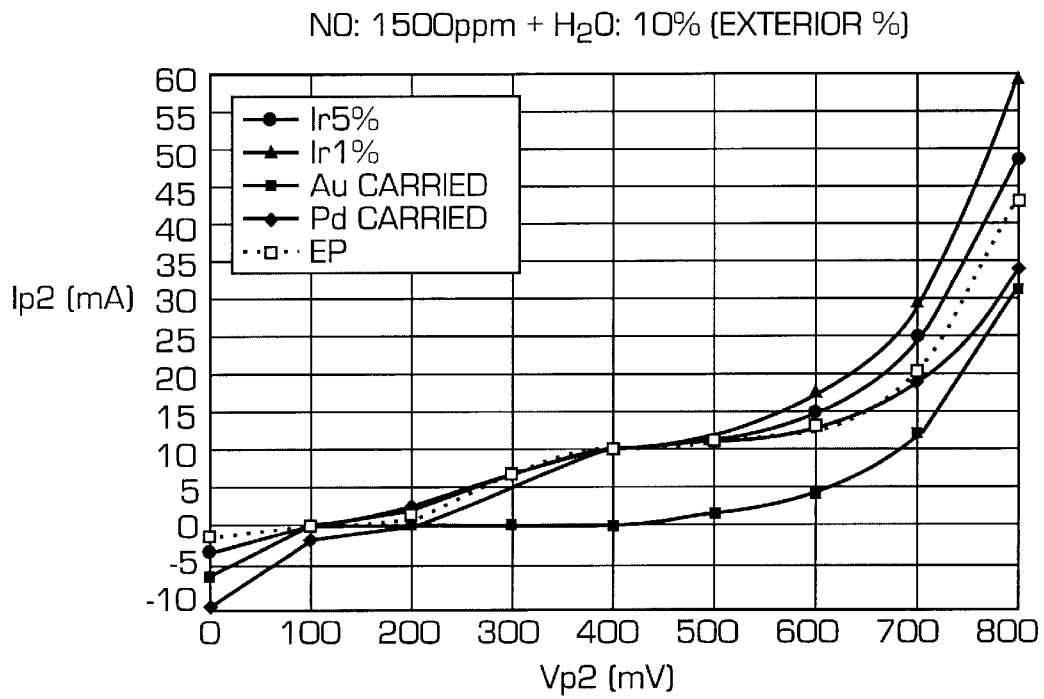
FIG. 7 is a graph showing the current characteristic of the second oxygen pump of each of the sensors according to an Example and Comparative Examples 1–4 (measurement gas containing 1500 ppm of NO is introduced).
Figure 8:
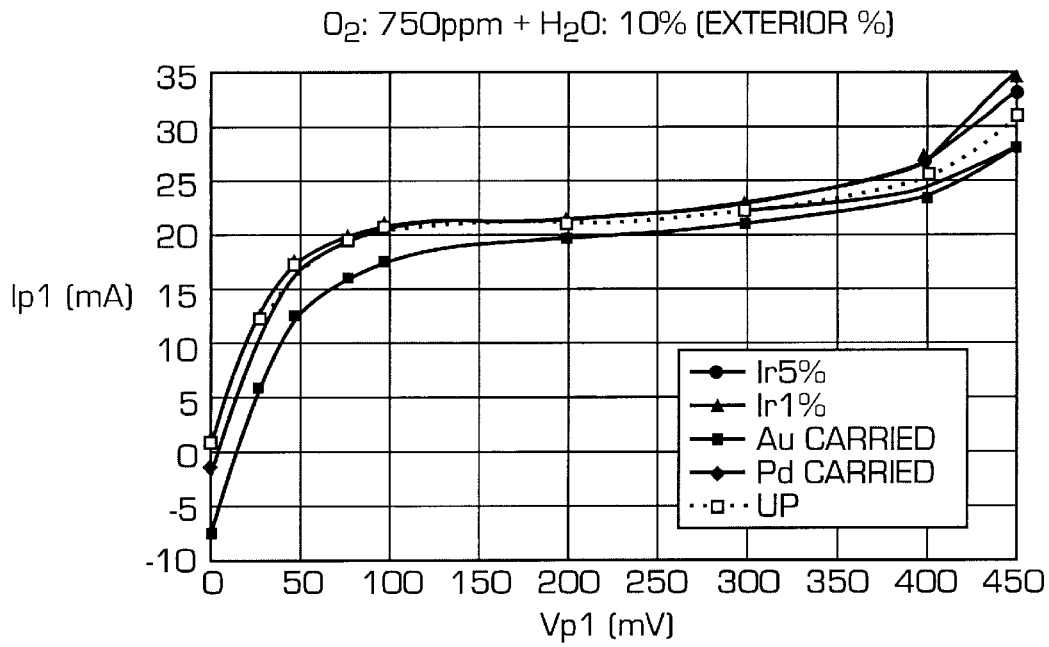
FIG. 8 is a graph showing the current characteristic of the first oxygen pump of each of the sensors according to an Example and Comparative Examples 1–3 and 5 (measurement gas containing 750 ppm of $O_2$ is introduced).
Figure 9:
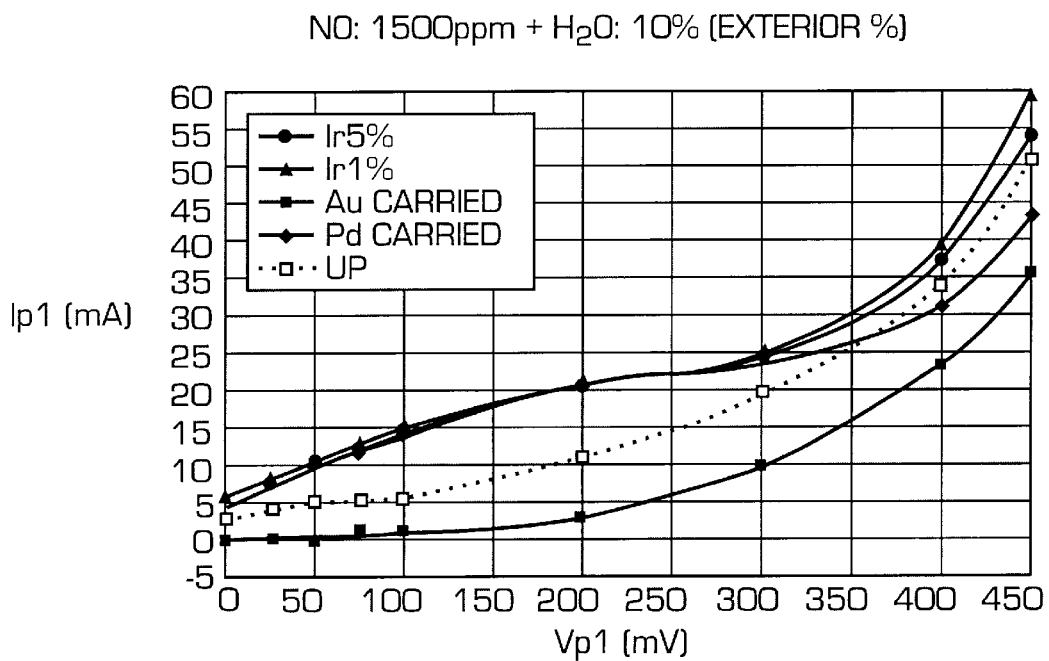
FIG. 9 is a graph showing the current characteristic of the first oxygen pump of each of the sensors according to an Example and Comparative Examples 1–3 and 5 (measurement gas containing 1500 ppm of NO is introduced).

A measurement gas having a predetermined concentration was supplied to each of the sensors of the Example and Comparative Examples 1–4, and the first oxygen pump current characteristic and second oxygen pump current characteristic were investigated. The measurement gas contained $H_2O$ (10%), $O_2$ (750 ppm) or NO (1500 ppm), and $N_2$ (balance). Further, heaters were disposed to sandwich the sensor from the sides thereof. The heater power was set to 21 W in order to heat the sensor for optimum operation. FIGS. 6 and 7 show the second oxygen pump current characteristics of the Example and Comparative Examples 1–4. FIGS. 8 and 9 show their first oxygen pump current characteristics. Although the Au-carrying electrode of the Example is slightly inferior to the Au-mixed electrode of Comparative Example 5 in terms of oxygen pump function (see FIG. 8), the $I_{P1}$ value is small even when NO of a predetermined concentration is added to the measurement gas, from which it is understood that dissociation of $NO_x$ is suppressed (see FIG. 9). Further, even when the Example is compared with Comparative Examples 1–4, it is found that the Au-carrying electrode of the Example has the strongest function of suppressing $NO_x$ dissociation. Since one electrode of the first oxygen-ion pump cell disposed within the first measurement chamber (see FIG. 1) must have a function of suppressing $NO_x$ dissociation, the Au-carrying electrode of the Example is superior to the electrodes of Comparative Examples 1–4. Since the electrode of the second oxygen-ion pump cell disposed within the second measurement chamber (see FIG. 1) must have a function of stimulating $NO_x$ dissociation, use of the Au-carrying electrode of the Example is not preferably used in the second measurement chamber. Also, FIG. 7 demonstrates that the sensor of the Example is characterized by a reduced variation in the second oxygen pump cell current $I_{P2}$ even when the voltage $V_{P2}$ applied to the second oxygen pump cell varies in a wide range, so that the output is stable, resulting in accurate measurement of $NO_x$ concentration. Accordingly, it is understood that the Au-carrying electrode of the Example provides a stable and enhanced function of suppressing $NO_x$ dissociation. Almost the same result is confirmed with Cu-carrying electrode, but not with Ag-carrying electrode.

The electrode according to the present invention enhances the function of suppressing $NO_x$ dissociation in the first measurement chamber of the $NO_x$-concentration sensor and stably provides the enhanced suppressing function. Thus, the output of the sensor becomes stable, which enables accurate measurement of a very low $NO_x$ concentration. In addition, according to the method of manufacturing electrodes of the present invention, firing is performed in a state in which Au and/or Cu fine particles are carried on particles of the solid electrolyte, so that a component having the function of suppressing $NO_x$ dissociation is finely and uniformly dispersed throughout the electrode. Therefore, the function of suppressing $NO_x$ dissociation is enhanced and stabilized.

What is claimed is:

1. A method of manufacturing an electrode of an $NO_x$-concentration sensor comprising:

a first measurement chamber into which a measurement gas is introduced via a first diffusion resistor;

an oxygen partial-pressure detection electrode for measuring a partial pressure of oxygen contained in the measurement gas within the first measurement chamber;

a first oxygen-ion pump cell having a pair of electrodes provided within and outside of the first measurement chamber, such that in response to a voltage applied between the pair of electrodes based on the electrical potential of the oxygen partial-pressure detection electrode, the first oxygen-ion pump cell pumps out oxygen within the measurement gas from the first measurement chamber to an extent such that $NO_x$ partially decomposes in said first measurement chamber, in an amount of not more than 30 wt. % of the $NO_x$ present;

a second measurement chamber into which the measurement gas is introduced from the first measurement chamber via a second diffusion resistor; and a second oxygen-ion pump cell having a pair of electrodes, one of which is provided inside the second measurement chamber, such that in response to a voltage applied between the pair of electrodes, the second oxygen-ion pump cell decomposes $NO_x$ within the second measurement chamber and pumps out the dissociated oxygen, so that a current corresponding to an $NO_x$ concentration flows through the second oxygen-ion pump cell, said method being adapted to manufacture the electrode provided inside the first measurement chamber among the pair of electrodes of the first oxygen-ion pump cell, and comprising the steps of:

impregnating, as a first constituent component, a solution containing one or more elements selected from the group consisting of Au and Cu into solid electrolyte powder having oxygen-ion conductivity;

drying and firing the solid electrolyte powder in order to obtain first-constituent-component carrying powder in which fine particles formed of the first constituent component are carried on the solid electrolyte powder;

mixing the first-constituent-component carrying powder with powder of one or more kinds of precious metal components selected from the group consisting of Pt, Pd, Rh, Ir and Re;

preparing a paste from the resultant mixed powder;

applying the paste onto a surface of a compact that becomes, after firing, a solid electrolyte layer constituting the first oxygen-ion pump cell; and firing the paste in order to form the electrode.

2. A method of manufacturing a gas sensor comprising:

a first measurement chamber into which a measurement gas is introduced via a first diffusion resistor;

an oxygen partial-pressure detection electrode for measuring a partial pressure of oxygen contained in the measurement gas within the first measurement chamber;

a first oxygen-ion pump cell having a pair of electrodes provided within and outside of the first measurement chamber, such that in response to a voltage applied between the pair of electrodes based on the electrical potential of the oxygen partial-pressure detection electrode, the first oxygen-ion pump cell pumps out oxygen within the measurement gas from the first measurement chamber to an extent such that a gas component partially decomposes in said first measurement chamber;

a second measurement chamber into which the oxygen-pumped out gas is introduced from the first measurement chamber via a second diffusion resistor; and a second oxygen-ion pump cell having a pair of electrodes, one of which is provided inside the second measurement chamber, such that in response to a voltage applied between the pair of electrodes, the second oxygen-ion pump cell decomposes a gas component within the second measurement chamber and pumps out the dissociated oxygen, so that a current corresponding to a gas component concentration flows through the second oxygen-ion pump cell, said method being adapted to manufacture the electrode provided inside the first measurement chamber among the pair of electrodes of the first oxygen-ion pump cell, and comprising the steps of:

impregnating, as a first constituent component, a solution containing one or more elements selected from the group consisting of Au and Cu into solid electrolyte powder having oxygen-ion conductivity;

drying and firing the solid electrolyte powder in order to obtain first-constituent-component carrying powder in which fine particles formed of the first constituent component are carried on the solid electrolyte powder;

mixing the first-constituent-component carrying powder with powder of one or more kinds of precious metal components selected from the group consisting of Pt, Pd, Rh, Ir and Re;

preparing a paste from the resultant mixed powder;

applying the paste onto a surface of a compact that becomes, after firing, a solid electrolyte layer constituting the first oxygen-ion pump cell; and firing the paste in order to form the electrode.

* * * * *